US005573767A

United States Patent [19]
Dufour et al.

[11] Patent Number: 5,573,767
[45] Date of Patent: Nov. 12, 1996

[54] METHOD FOR IMPROVING THE ORGANOLEPTIC QUALITIES OF THE MEAT FROM UNCASTRATED MALE DOMESTIC ANIMALS, VACCINES WHICH ARE USABLE IN THIS METHOD, NEW PEPTIDE, IN PARTICULAR FOR PRODUCING THESE VACCINES AND VACCINATION KIT RELATING THERETO

[75] Inventors: Raymond Dufour, Lyons; Claude Roulet, Venissieux; Claire Chouvet, Lyons; Michel B. Bonneau, Montfort, all of France

[73] Assignee: Societe Anonyme, Lyons, France

[21] Appl. No.: 343,883

[22] Filed: Nov. 17, 1994

Related U.S. Application Data

[63] Continuation of Ser. No. 946,495, Nov. 9, 1992, abandoned.

[30] Foreign Application Priority Data

Mar. 1, 1991 [FR] France ................................ 91 02513
Dec. 10, 1991 [FR] France ................................ 91 15289

[51] Int. Cl.$^6$ ...................... A61K 38/09; A61K 39/385; C07K 7/23
[52] U.S. Cl. .................... 424/195.11; 424/184.1; 424/185.1; 424/194.1; 530/313
[58] Field of Search ............................ 424/130.1, 184.1, 424/194.1, 195.11, 185.1; 530/313

[56] References Cited

U.S. PATENT DOCUMENTS

| | | |
|---|---|---|
| 4,010,125 | 3/1977 | Schally . |
| 4,018,726 | 4/1977 | Schally . |
| 4,024,121 | 5/1977 | Schally . |
| 4,556,555 | 12/1985 | Esbenshade . |
| 4,608,251 | 8/1986 | Mia ....................................... 424/185.1 |
| 4,676,981 | 6/1987 | Silversides et al. ................. 424/145.1 |
| 4,770,874 | 9/1988 | Allison et al. ........................ 424/278.1 |
| 4,975,420 | 12/1990 | Silversides et al. ............... 424/195.11 |
| 5,036,047 | 7/1991 | Mia ....................................... 424/185.1 |
| 5,484,592 | 1/1996 | Meloen et al. ........................ 424/185.1 |

FOREIGN PATENT DOCUMENTS

| | | |
|---|---|---|
| 0181236 | 5/1986 | European Pat. Off. . |
| 0293530 | 12/1988 | European Pat. Off. . |
| 0309863 | 4/1989 | European Pat. Off. . |
| 8606635 | 11/1986 | WIPO . |
| WO88/00056 | 1/1988 | WIPO . |
| WO88/01176 | 2/1988 | WIPO . |
| WO88/05308 | 7/1988 | WIPO . |
| WO90/03182 | 4/1990 | WIPO . |
| WO90/11298 | 10/1990 | WIPO . |

OTHER PUBLICATIONS

Arimura et al (1975) Acta Endocrinologica 78:222–231.
Talwar (1985) J. Steroid Biochem. 23(5B):795–800.
Silversides et al (1988) J. Reproductive Immunol 13:249–261.
Carelli et al (1985) Int. J. Immunopharmc. 7(2):215–224.
Lobley et al (1992) Anim. Prod. 55:193–202.
"Responses of ram lambs to active immunization against testosterone and luteinizing hormone–releasing hormone", Schanbacher, B. D., Am. J. Physiol., 1982, 242, pp. 201–205.
"Short Communications", Roberston, I. S., The Veterinary Record, Dec. 15, 1979, pp. 556–557.
"Production of Antiserum to LH–Releasing Hormone (LH–RH) Associated with Gonadal Atrophy in Rabbits: Development of Radioimmunoassays for LH–RH", Arimura, A. et al, Endocrinology, 1973, pp. 1092–1103.
"Immunisation active de porc male contre la gonadoliberine: effets sur la secretion d'hormones gonadotropes et sur la teneur en 5 α–androst–16–ene–3–one du tissu adipeux", Caraty, Alain et al, C.R. Acad. Sc. Paris t. 303, Serie III, (1986). abstract translated.
"Effect of Active Immunization To Luteinizing Hormone Releasing Hormone on Serum and Pituitary Gonadodotrophins, Testes and Accessory Sex Organs", Fraser, H. M. et al, J. Endocr., (1974), 63, 399–406.
"Effect of Active Immunization Against LHRH or LH in Boars: Reproductive Consequences and Performance Traits", Falvo, R. E., J. Anim. Sci., 1986, 63, pp. 986–994.
"Utilization of the Intact Male For Red Meat Production: A Review", Seideman, S. C. et al, Journal of Animal Science, vol. 55, No. 4, 1982, pp. 826–840.
"Reversal of the Inhibitory Action of an Antiserum To Luteinizing Hormone Releasing Hormone (LH–RH) By An Inactive Fragment of LH–RH", Fraser et al, J. Endocr., (1977), 73, pp. 393–394.
"Effect of Active Immunisation of Ewes Against Synthetic Luteinising Hormone Releasing Hormone", Jeffcoate et al, Theriogenology, Oct. 1978, vol. 10, No. 4, pp. 323–335.
"Immunological castration of male mice by a totally synthetic vaccine administered in saline", Carelli et al, Proc. Natl. Acad. Sci, vol. 79, pp. 5392–5395, Sep. 1982.
"Ovulation Blockage in Rats By Rabbit Anti–Luteinizing Hormone Releasing Factor Serum", Makino, T. et al, Contraception, Aug. 1973, vol. 8, No. 2, pp. 133–145.

(List continued on next page.)

Primary Examiner—Kay K. A. Kim
Attorney, Agent, or Firm—Larson and Taylor

[57] ABSTRACT

Method for improving the organoleptic qualities of the meat from uncastrated male domestic animals, vaccines which are usable in this method, new peptide, in particular, for producing these vaccines and vaccination kit relating thereto.

The method for improving the organoleptic qualities, especially the smell, taste and tenderness, of the meat from uncastrated male domestic animals comprises, shortly before slaughter of the animal in question, abolition of the action of the androgenic and non-androgenic steroids by active or passive anti-LHRH immunoneutralization, while the advantages linked to the male character of the animal are maintained virtually up to slaughter. The vaccines comprise, as a peptide, natural LHRH or a peptide of formula Trp - Ser - Tyr - Gly - Leu - Arg - Pro - Gly - $NH_2$, coupled to an immunogenic carrier protein.

18 Claims, No Drawings

OTHER PUBLICATIONS

"Interet et limites de la production de viandes de porc male entier", Bonneau, M., *INRA Prod. Anim.,* 1988, 1(2), pp. 133–140.

"Neutralization of Pheromones By Antisera in Pigs", Claus, R., *Immunization with Hormones in Reproduction Research,* 1975, North–Holland Publishing Co., pp. 193–194.

"Immunization Against 5α–Androstenone in Boars", Williamson et al, *Livestock Production Science,* 12 (1985) pp. 251–264.

Oonk et al (27–29 Sep. 1995) Proceedings of a Meeting of the EAAP Working Group, "Production and Utilisation of Meat from Entire Male Pigs" Milton Keynes UK pp. 1–5.

METHOD FOR IMPROVING THE ORGANOLEPTIC QUALITIES OF THE MEAT FROM UNCASTRATED MALE DOMESTIC ANIMALS, VACCINES WHICH ARE USABLE IN THIS METHOD, NEW PEPTIDE, IN PARTICULAR FOR PRODUCING THESE VACCINES AND VACCINATION KIT RELATING THERETO

This application is a continuation of application Ser. No. 07/946,495 filed Nov. 9, 1992 now abandoned.

The present invention relates to a method for improving the organoleptic qualities, especially the smell, taste and tenderness, of the meat from uncastrated male domestic animals, in particular male cattle, sheep and pigs.

The invention also relates to vaccines which are usable in this method, to a new peptide for producing such vaccines and to a vaccination kit relating thereto.

The advantages of using the intact male over the castrated male in the fattening of domestic animals intended for meat production have been stressed for several decades by specialists in zootechnics. They relate to a higher growth rate, especially in cattle and sheep, to a better utilization of the feed ration and to a carcass which is leaner but better endowed with muscle mass in all domestic species (S. C. SEIDEMAN et al., J., of Animal Science, 1982, 55 (4) 826–840 and M. BONNEAU, INRA Prod. Anim., 1988, 1 (2) 133–140).

The main drawbacks of this use of the intact male, pointed out in the reviews cited above, relate to the unpleasant smell and taste in the case of male pigs and sheep and the less tender meat from intact male cattle and sheep, and justify the current practices of surgical castration.

In effect, while androgenic steroids including androstenediol, androstenedione and testosterone are the decisive factors in the advantages expected in all domestic species for a faster growth and a better utilization of the feed ration, they are held responsible for the less tender meat from intact male cattle and sheep. The non-androgenic steroids or 16-androstene derivatives including 5αandrostenone (5αandrost-16-en-3-one), in the male pig, are partially responsible for the unpleasant smell and taste of the meat from a number of intact male pigs once they have reached puberty, these factors detracting from the quality of the meat and being an obstacle to its marketing in the fresh state.

Skatole, a product derived from tryptophan and produced by the intestinal microbial flora, is a compound partially responsible for the unpleasant smell and taste of the meat from the intact male pig. Its production depends on environmental, nutritional and breed factors. Its accumulation in the adipose tissue is greater in the boar and is considered to be linked to the secretion of gonadal sex steroids.

For experimental purposes, an attempt has already been made to decrease or abolish the development of the male character in young animals or the secretion of testicular hormones, in particular testicular steroids, by active or passive immunoneutralization against these or against the hormones participating in their secretion, in particular luteinizing hormone or LH and the hormone gonadoliberin (GnRH), also known as luteinizing hormone releasing hormone (LHRH). Tests have also been conducted on pigs to lower the tissue level of 5αandrostenone, of the 16αandrostene group, by active immunization directed towards this compound (E. D. WILLIAMSON et al., Livestock Production Science, 1985, 12, 251–264) or by passive immunization against this same compound (R. CLAUS, Immunization with Hormones in Reproduction Research, ed. Nieschlag, 1975). It is possible to seek to abolish or decrease the secretion of testicular steroids by immunoneutralization of the gonadotropic hormone LH specific to the species in question (R. E. FALVO et al., J. Anim. Science, 1986, 63, 986–994), or by anti-LHRH immunoneutralization of endogenous LHRH. Only active anti-LHRH immunization has been recommended by various authors. In pigs, the lowering of αandrostenone has been obtained by this method (A. CARATY and M. BONNEAU, C.R. Acad. Sci. Paris 1986, 303, Series III (16) 673–676; R. E. FALVO et al., J. Anita. Sci., 1986, 63, 986–994).

In sheep, B. D. SCHANBACHER (Am. J. Physiol., 1982, 242, E201–E205) recommends anti-LHRH immunization to delay testicular development and produce a castration effect in male lambs. In cattle, P. S. ROBERTSON (Vet. Rec., 1979, 105, 516–517) describes an anti-LHRH immuno-logical castration.

The anti-LHRH immunoneutralization tests described on laboratory animals (ARIMURA et al., Endocrinology, 1973, 93, 1092–1103; FRASER H. M. et al., J. Endocr. 1974, 63, 399–406; MAKINO T. et al., Contraception, 1973, 8 (2), 133–145; CARELLI C. et al., Proc. Natl. Acad. Sci., USA, 1982, 79, 5392–5395) and on several domestic species (JEFFCOATE et al., Theriogenology, 1978, 10(4), 323–335; ROBERTSON I. S. et al., Veterinary Record, 1979, 105, 556; SCHANBACHER B. D. Am. J. Physiol., 1982, 242, E201-E205) have shown that it is possible to obtain arrest of testosterone secretion, weight regression of the testicles and its appended glands, arrest of spermatogenesis and, at behavioral level, disappearance of libido.

This work has led to the suggestion of recourse to an early immunoneutralization, in particular anti-LHRH, to replace the traditional surgical castration for breeding purposes.

In U.S. Pat. No. 4,556,555, a method is thus described for passive immunization of animals before puberty, using an antiserum containing antibodies directed towards gonadotropin.

International Patent Application WO 90/11,298 describes a method of anti-LHRH immunization at birth, using 2 LHRH sequences in tandem coupled to a carrier protein, to improve meat quality in pigs.

International Patent Application WO 88/00,056 describes a method of anti-LHRH immunological castration intended for improving the social and sexual behavior of male animals as a replacement for surgical castration which affects the growth rate. The bulls are vaccinated at the age of 8 to 40 weeks and then receive several boosters.

An anti-LHRH vaccine sold under the brand name VAX-STRATE by the Australian company WEBSTERS is used in cows.

R. E. Falvo et al., (J. Anim. Sci. 1986, 63 : 986–994) have immunized several groups of boars using LHRH-human serum globulin conjugates in Freund's complete adjuvant or with muramyl peptide as adjuvant. After vaccination and several boosters, the authors observed high titers of anti-LHRH antibodies, but with the need to perform repeated boosters in order to maintain the high antibody titer.

I. S. Robertson describes a method of immunization with LHRH conjugated to tetanus anatoxin or to thyro-globulin, and suggests that the immunological approach would permit a late castration with the advantages which may be expected from the standpoint of weight gain. He 10 concludes, however, that there are still efforts to be made in order to arrive at a castration method which is usable in practice, both in respect of the method itself and of the adjuvant, Freund's adjuvant being prohibited in practice.

Lastly, A. Caraty and M. Bonneau (C.R. Acad. Sc. Paris, vol. 303, Series III, No.16, 1986) have performed an anti-LHRH immunization in male pigs. The authors suggest that the blockade of steroid production 2 to 3 weeks before slaughter would enable the high potential of this type of animal for meat production to be exploited while avoiding the problems created by the accumulation of androsterone in the adipose tissue. They conclude, however, that substantial progress remains to be made in the immunization techniques before it is possible to propose active anti-LHRH immunization as a technique which is usable in pig farming.

Moreover, late immunoneutralization creates in practice the considerable problem of the safety of the treatment, and in particular of the local reactions engendered by the vaccines, especially oily vaccines, with the risks of rejection or of downgrading of the meat resulting therefrom.

Improvement of the organoleptic qualities in cattle and sheep has not been suggested.

The Applicant has, in point of fact, found an industrially applicable method which enables the organo-leptic properties of the meat from animals to be improved, in which method, shortly before slaughter of the animal, the action of the androgenic and non-androgenic steroids is substantially abolished by active or passive anti-LHRH immunoneutralization, while the advantages due to the male character of the animal are maintained virtually up to slaughter.

According to a first preferred embodiment of this method, an anti-LHRH vaccine is administered to the animal, preferably in emulsion form, preferably during or before the phase of fattening of the animal, and then, shortly before slaughter of the animal, an anti-LHRH vaccine is administered again. The procedure may be accomplished in two separate administrations, or by means of a controlled-release method.

In pigs, it is especially advantageous to administer, before slaughter, the anti-LHRH vaccine with an aqueous type adjuvant, in particular aluminum hydroxide gel and/or saponin.

This administration is preferably performed 15 to 21 days before slaughter.

In contrast, in cattle and, where appropriate, in sheep, the administration preceding slaughter is preferably carried out with an adjuvant in emulsion form, and preferably 1 to 2 months before slaughter. This administration is preferably performed at least 4 weeks, and preferably several months, after the first administration.

In any case, for the vaccine in emulsion form intended for the first administration and, in cattle, for the second administration, it is preferable for the vaccine to take the form of a water-in-oil emulsion. However other forms of emulsion may be envisaged.

This vaccine, preferably of the emulsion type, is designed, according to the invention, to induce a primary, low-intensity immune response without a significant or even measurable effect on gonadal steroid secretion. The formulation as an emulsion is preferred, but other formulations are usable as long as they produce the same effect.

The administration which precedes slaughter is carried out with a vaccine formulated to produce, at this time, the abolition or a significant lowering of steroid secretion without an adverse local or general reaction capable of impairing the appearance or quality of the meat.

Preferably, in particular for pigs, the conjugate, in aqueous solution, is put into the following two formulations: the first, in the form of a stable water-in-oil emulsion made from a mixture of highly purified mineral, animal or vegetable oils and of non-ionic surfactants, for inducing a low-intensity immune response without a measurable effect on gonadal steroid secretion, and the second, not emulsified, with aluminum hydroxide gel and saponin, triggering a rapid and intense immune reaction resulting in sufficient production of neutralizing anti-LHRH antibodies to bring about the decrease in or abolition of gonadal steroids and the decrease in the associated transport of skatole of intestinal origin.

The emulsion used is, in distinction to that which is obtained using Freund's complete or incomplete adjuvant, a stable emulsion enabling a ready-to-use vaccine to be prepared. The inflammatory skin reaction remains very weak and localized at the points of administration of the two vaccine formulations, and manifests itself in the form of well-circumscribed papules on external examination. Its internal development remains limited to the superficial dermis. It disappears without leaving an apparent granuloma at the time of slaughter of the animals.

According to another embodiment of this method, hyperimmune anti-LHRH serum or plasma or alternatively anti-LHRH monoclonal antibodies is/are administered to the animal a few days before slaughter, in particular 5 to 15 days beforehand.

The passive anti-LHRH immunization bringing about the decrease in or even the abolition of androgenic and non-androgenic steroid secretion was obtained by intra-muscular administration of hyperimmune equine plasma. Brought to a sufficient level, measured by the LHRH antibody titer of the serum of the recipient animal, this immunization brings about a decrease in plasma testosterone from day 3 onwards; maintained at the same level for the following 12 days, it is sufficient to bring about a lowering of the tissue androsterone to below 0.50 microgram/g, at which value the unpleasant smell and particular taste of male pig meat would no longer be perceived by the consumer. This passive immunization method has shown that maintenance of the significant decrease in testosterone for 12 days is sufficient to lower the tissue androsterone concentration to below the set threshold. This passive immunization can be envisaged by the use of anti-LHRH monoclonal anti-bodies secreted by porcine hybridomas or heterohybridomas.

The mode of administration of these formulations is preferably transcutaneous, in particular using a needleless injection apparatus, via a jet under pressure, in particular according to Patent Application FR-A-2,652,257.

The method according to the invention has the great advantage of being completely safe, in particular of not inducing local reactions liable to lead to down-grading of the meat.

The inflammatory skin reaction remains localized at the points of administration of the two vaccine formulations, and manifests itself in the form of well-circumscribed papules on external examination. Its internal development remains limited to the superficial dermis. It disappears without leaving an apparent granuloma at the time of slaughter of the animals. The inflammatory reaction, limited in time and to the points of administration, reflects the tolerance to the two vaccine formulations and is obtained by the transcutaneous administration of these, performed using a needleless injector.

The anti-LHRH immunization necessitates conjugation of the LHRH peptide or a fragment of the LHRH peptide, which is non-immunogenic under economical conditions for their use, to an immunogenic protein, termed carrier, via a covalent bond.

LHRH or GnRH, whether natural or synthetic, is composed of 10 amino acids, numbered from 1 to 10 proceeding from the amino-terminal terminus to the carboxy-terminal terminus, according to the following formula:

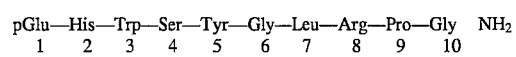

These symbols by convention represent: pGlu, pyroglutamic acid; His, histidine; Trp, tryptophan; Ser, serine; Tyr, tyrosine; Gly, glycine; Leu, leucine; Arg, arginine; Pro, proline.

Anti-LHRH immunogenic conjugates, described by the various authors, may be produced, as regards the hapten, with:

a) whole LHRH or LHRH modified in one or more of its parts to obtain the desired amino-terminal, carboxyterminal or intermediate conjugation, b) one of its peptide fragments composed of 5 to 7 amino acids, modified or otherwise, to obtain the desired amino-terminal, carboxy-terminal or intermediate conjugation, c) an agonist bearing a substituted amino acid, most commonly at position 6, to obtain an intermediate conjugation.

As regards the carrier protein, bovine serum albumin, human serum albumin, thyroglobulin, ovalbumin and human or equine globulins have been used.

Thus, European Patent Application EP-A-181,236 describes immunogenic conjugates comprising a nonapeptide or decapeptide including a sequence, corresponding to the last 8 amino acids of the LHRH molecule, to which a lysine or a cysteine-lysine sequence is added on the amino-terminal side.

Moreover, Patent Application WO 88/05,308 discloses conjugates, made using fragments of 5, 6 or 7 adjacent amino acids of the natural molecule, in which each fragment includes the N-terminal pyroglutamic acid or the carboxy-terminal glycinamide and to which an additional amino acid or amino acid sequence can be added to the end linked to the immunogenic protein.

The conjugating agents used may be classified in three major categories: activating agents, homo-bifunctional agents and heterobifunctional agents. Whereas, with activating agents, the link between the two molecules is made between two functions already present, with the others, the link is made via a hydrocarbon residue termed ligand.

Among activating agents, there may be mentioned periodic acid, employed to oxidize the oligosaccharide residues of the glycoproteins to aldehydes, with which the amine groups of the other molecule participating in the conjugate will subsequently react.

Carbodiimides are activating agents widely employed for the coupling of antigens to proteins, and among these the most extensively used is certainly N-ethyl-N'-(3-dimethylaminopropyl)carbodiimide (EDC) hydrochloride, which enables the reaction to be performed in an aqueous medium. Their action leads to the formation of an amide bond between a carboxyl group of one protein, activated in the form of an intermediate O-alkylisourea, and an amine group borne by another molecule. Their advantage lies in their simplicity of use.

Homobifunctional agents are molecules which possess two identical reactive groups separated by a hydrocarbon chain. Among these there may be mentioned glutaraldehyde, which reacts with two primary amine groups, alkyl or aryl diisothiocyanates, which react with primary amines and thiols, and bisdiazotized benzidine, which couples with the aromatic residues of tyrosine. Bismaleimides and bisamidinates may be mentioned for the record. The major drawback of homobifunctional agents is that of poor control over the nature of the conjugates formed, since these agents can react with two molecules of the same nature and lead to the formation of oligomers or polymers.

To remedy this, chemists have introduced heterobifunctional agents, in which the two groups have different specificities. In the general case, one of these groups is an N-hydroxysuccinimide ester which, under mild conditions, reacts with the free amine groups of proteins to give, on the one hand N-hydroxysuccinimide, and on the other hand the protein bearing via a covalent amide bond the coupling agent on which the 2nd function occurs. From a rather general standpoint, the latter can react with thiols supplied by the molecule to be coupled, these thiols being either initially present in the molecule in the form of cysteine residues (it being possible for the latter to be natural constituents or, in the case of peptides, introduced intentionally during synthesis), or supplied by agents such as 2-iminothiolane or N-[3-(2-pyridyldithio)propanoyloxy]succinimide(SPDP), after reduction.

Among the possibilities stated above, it is preferable to use whole LHRH. In this case, natural LHRH is preferred to agonists such as (D-Lys$^6$)-LHRH by comparison of the immunogenic activity of the conjugates prepared with these two peptides.

The carbodiimide is preferred to glutaraldehyde as an agent for conjugating natural-form LHRH with alpha-globulin.

Human or equine alpha-globulin, fraction IV-1 or IV-4, is preferred to human or bovine serum albumin.

Preferably, the vaccines comprise one and the same active principle, preferably comprising an alpha- globulin-LHRH conjugate; the LHRH is preferably in natural form and the alpha-globulin of human or equine origin, in particular fractions IV-1 and/or IV-4. The conjugate is preferably obtained by adding from 0.5 to 2 volumes of a 2.5% solution of N-ethyl-N'-(3-dimethylaminopropyl)carbodiimide (EDC) hydrochloride in 0.9% NaCl to 1 volume of alpha-globulin/LHRH mixture in solution con-raining 2 to 20 mg/ml in 0.9% NaCl. After stirring, the mixture is left overnight and then purified by gel permeation chromatography.

As regards the carrier protein, it is possible to use serum albumins, in particular bovine or human, thyroglobulin, ovalbumin, human or equine globulins, and anatoxins, in particular tetanus anatoxin.

The predominance of the immune response of male pigs to the carboxy-terminal fraction of the LHRH peptide conjugated with the carbodiimide, or of its agonist (D-Lys$^6$)-LHRH conjugated with SPDP, to alpha-globulin, which was observed, led to the definition of an anti-LHRH immunogenic conjugate employing an advantageous peptide possessing the carboxy-terminal terminus of LHRH.

Consequently, according to a second preferred embodiment of the invention, the Applicant found that it was very advantageous to use a new peptide comprising the last 8 amino acids of LHRH, that is to say a decapeptide of formula:

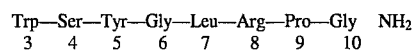

$$\text{Trp—Ser—Tyr—Gly—Leu—Arg—Pro—Gly} \; NH_2$$
$$\phantom{Trp}3 \phantom{xx} 4 \phantom{xxx} 5 \phantom{xxx} 6 \phantom{xxx} 7 \phantom{xxx} 8 \phantom{xxx} 9 \phantom{xx} 10$$

which possesses great immunogenic activity without displaying the hormonal activity of natural LHRH.

A subject of the invention is hence this new peptide (3–10), and the conjugates incorporating it, coupled to an immunogenic carrier protein among those mentioned above, ovalbumin and equine alpha-globulin, in particular fractions IV-1 and/or IV-4, being preferred.

In the invention, the carbodiimide is preferred to glutaraldehyde and to heterobifunctional agents as an agent for conjugating the LHRH (3–10) peptide, in particular to equine alpha-globulin or ovalbumin.

In the preferred preparation of conjugate, LHRH (3–10) and the carrier protein, ovalbumin or alpha-globulin, are dissolved in the proportion of 2 to 40 mg per ml each in 0.1M NaCl/0.1M 2-(N-morpholino)ethane-sulfonic acid buffer. 0.5 to 2 volumes of a 2.5% solution of N-ethyl-N'-(3-dimethylaminopropyl) carbodiimide in the same buffer are then added. The pH is adjusted by adding 1N sodium hydroxide. After stirring, the mixture is left overnight and is then purified by gel permeation chromatography, which removes uncoupled LHRH (3–10), residual carbodiimide and its hydrolysis products.

A subject of the invention is also the new anti-LHRH vaccines employing such conjugates as active principle, which are usable for the method according to the invention.

A subject of the invention is also the passive anti-LHRH (3–10) immunization in accordance with the method described above.

It also relates to kits combining, in a single pack, an equal number of doses of vaccine to be administered before slaughter and of vaccine to be administred in a primary injection. Preferbaly, these vaccines are packaged in a reduced volume and at an increased concentration for administration by transcutaneous jet, for example according to the French patent application cited above.

The invention will now be described in greater detail by means, on the one hand of tests comparing several products and methods of vaccination according to the invention, and on the other hand of tests which showed the predominance of the immune response of male pigs to the carboxy-terminal fraction of the LHRH peptide and of the test of anti-LHRH vaccination performed on male pigs according to the invention.

I - Use of Whole LHRH

A. Greater Immunogenic Activity of the Conjugate Maintaining Intact the Most Extensive Carboxy-terminal Fraction of the LHRH Peptide, and Choice of the Conjugate Based on Natural-Formula LHRH in Preference to that Obtained Using the Agonist (D-Lys$^6$)-LHRH A1. - Anti-LHRH immunization of intact male pigs and of OFA male rats.

The comparison of activity of two anti-LHRH vaccines consisting of conjugates between natural-form LHRH (B1 and B2) or (D-Lys$^6$)-LF-RH (A1 and A2) and human albumin, the conjugates being obtained with carbodiimide in the aqueous phase and SPDP, respectively, put into an oil-in-water emulsion and administered intramuscularly in pigs and subcutaneously in rats, leads to the following conclusions:

Greater activity of the vaccine based on natural-form LHRH: mass of the conjugated LHRH peptide lower than that of the conjugated (D-Lys$^6$)-LHRH peptide for a recruitment of a larger number of animals displaying an immune response (Tables 1 and 3).

Dose effect which manifests itself in a recruitment of a higher number of animals displaying an immune response with the same conjugate (Table 3).

A1.1 - Preparation of (D-Lys$^6$) -LHRH-albumin conjugates with SPDP.

The preparation of (D-Lys$^6$)-LHRH-albumin conjugates is carried out in three steps: preparation of {N-[3-(2-pyridyldithio)propanoyl]-D-Lys$^6$}-LHRH, preparation of N-(3-mercaptopropanoyl)albumin, then coupling.

{N-[3-(2-Pyridyldithio)propanoyl]-D-Lys$^6$}-E is prepared by reacting an excess of SPDP with LHRH in aqueous solution (6 mol of SPDP per mole of LHRH), and then, after one night at 4° C., centrifuging the product obtained. The latter is dissolved in 8M urea and the 2-pyridyldithio groups present are assayed.

N-(3-Mercaptopropanoyl)albumin is obtained by the action of 0.2 mmol of SPDP on 1 g of human albumin dissolved in 100 ml of 0.1M phosphate buffer, and then, after one night of contact at 4° C. and acidification to pH 6, by reduction with dithiothreitol. It is then purified by gel filtration chromatography. Assay of thiol and protein yields the average level of substitution.

Coupling is performed taking one 2-pyridyldithio group per 1.25 thiol groups. The pH is taken to 7–7.5 and then, after one hour, the yield is determined by measurement of the 2-pyridinethione liberated.

The average level of substitution is deduced from this. Finally, the conjugate is purified by chromatography and concentrated by ultrafiltration.

A1.2 - Preparation of the LHRH-Albumin conjugate with carbodiimide.

1000 mg of N-ethyl-N'-(3-dimethylaminopropyl)-carbodiimide hydrochloride, dissolved immediately before use in 40 ml of 0.9% NaCl, are added to 300 mg of LHRH and 300 mg of human albumin dissolved in 30 ml of 0.9% NaCl. After stirring, the mixture is left overnight at room temperature protected from light. It is then chromatographed on a Sephadex G-50 gel; the fractions corresponding to the conjugate are collected, where appropriate concentrated and frozen.

From the fractions containing uncoupled LHRH, the amount of uncoupled LHRH and hence the average level of conjugation are determined. The latter is reproducible and varies from 8 to 10 mg of LHRH coupled per 100 mg of albumin.

From the UV spectra of the conjugate before and after chromatography, the chromatographic yields of conjugate and hence the amount (or concentration) of LHRH conjugated are deduced.

A1.3 - Assay techniques

The antibody titer is determined according to the technique described by JEFFCOATE et al., Acta. Endocr., Copenh., 1974, 75: 625–635.

Testosterone is assayed directly on plasma by an RIA technique employing the radioligand testosterone C19-carboxymethyl ether-[$^{125}$I]histamine.

Binding to the labelled peptide is determined after labelling the various peptides with iodine-125 according to COPPOLAND et al., Endocr., 1979 104: 1504–1506 and determination according to the technique described by JEFFCOATE et al., Acta Endocr., Copenh., 1974, 75, 625–635.

A1.4 - Illustrations

Tests on rats

Table no. 1: anti-LHRH antibody response measured by the degree of binding of iodine-125–1-labelled LHRH Table no. 2: effect of anti-LHRH immunization on plasma testosterone concentration Dosage Vaccines A1: 50 µg of conjugated (D-Lys$^6$)-LHRH B1: 12 µg of conjugated LHRH Tests on intact male pigs Table no. 3: anti-LHRH antibody response measured by the degree of binding of iodine-125–1labelled LHRH Dosage Vaccines A1: 0.5 mg of conjugated (D-Lys$^6$)-LHRH A2: 6 mg of conjugated (D-Lys$^6$) -LHRH B1: 0.15 mg of conjugated LHRH B2: 1.20 mg of conjugated LHRH

TABLE 1

Anti-LHRH antibody response measured by the degree of binding of iodine-125-labelled LHRH
TESTING FOR ANTIBODIES (% Bo/T) IN THE SERUM (1/100) IN RATS

| INJECTIONS | TIME (WKS) | GROUP A1 50 µg Dlys6-LHRH/ HSA/AE1 | GROUP B1 12 µg LHRH/ EDC/HSA/AE1 | TITER B/T = 50% |
|---|---|---|---|---|
| SC | 0 | — | — | — |
|  |  | — | — | — |
|  |  | — | — | — |
| SC | 4 | 0.0 | 15.4 | <100 |
|  |  | 7.8 | 7.6 | <100 |
|  |  | 0.0 | 35.3 | <100 |
|  |  | 0.0 | 51.1 | 100 |
|  | 5 | 4.3 | 91.1 | 1600 |
|  |  | 14.1 | 85.3 | 980 |

TABLE 1-continued

Anti-LHRH antibody response measured by the degree of binding of iodine-125-labelled LHRH
TESTING FOR ANTIBODIES (% Bo/T) IN THE SERUM (1/100) IN RATS

| INJEC-TIONS | TIME (WKS) | GROUP A1 50 μg Dlys6-LHRH/ HSA/AE1 | GROUP B1 12 μg LHRH/ EDC/HSA/AE1 | TITER B/T = 50% |
|---|---|---|---|---|
|  |  | 5.9 | 70.8 | 270 |
|  |  | 15.8 | 94.9 | 2100 |
|  | 6 | 0.0 | 64.3 | 120 |
|  |  | 11.3 | 67.9 | 220 |
|  |  | 11.7 | 96.1 | 2400 |
|  |  | 0.0 | 68.3 | 280 |
|  | 7 | 14.5 | 72.5 | 400 |
|  |  | 0.0 | 92.4 | 2100 |
|  |  | 0.0 | 64.2 | 200 |
|  |  | 11.5 | 67.2 | 240 |
|  | 8 | 19.6 | 70.4 | 310 |
|  |  | 0.0 | 98.8 | 3200 |
|  |  | 9.2 | 68.7 | 2200 |
|  |  | 0.0 | 38.8 | 310 |

TABLE 2

Effect of anti-LHRH immunization on plasma testosterone concentration
ASSAY OF PLASMA TESTOSTERONE (NG/ML) IN RATS

| INJEC-TIONS | TIME (WKS) | CON-TROLS | GROUP A1 50 μg Dlys6-LHRH/ PDP/HSA | GROUP B1 12 μg LHRH/ EDC/HSA |
|---|---|---|---|---|
| SC | 0 | 0.40 | — | — |
|  |  | 0.26 | — | — |
|  |  | 0.47 | — | — |
|  |  | 0.00 | — | — |
| SC | 4 | 2.25 | 4.16 | 2.51 |
|  |  | 1.05 | 5.83 | 2.38 |
|  |  | 2.34 | 4.43 | 3.63 |
|  |  | — | 4.17 | 0.58 |
|  | 5 | 3.80 | 2.99 | 0.00 |
|  |  | 1.76 | 2.33 | 0.00 |
|  |  | 5.05 | 2.85 | 0.00 |
|  |  | 6.67 | 1.54 | 0.00 |
|  | 6 | 2.01 | 3.26 | 0.00 |
|  |  | 4.47 | 0.09 | 0.00 |
|  |  | 4.69 | 1.10 | 0.00 |
|  |  | 1.96 | — | 0.00 |
|  | 7 | 2.28 | 1.32 | 0.00 |
|  |  | 1.92 | 0.89 | 0.00 |
|  |  | 1.89 | 1.59 | 0.00 |
|  |  | 1.65 | 2.17 | 0.00 |
|  | 8 | 0.97 | 1.75 | 0.00 |
|  |  | 1.91 | 1.48 | 0.00 |
|  |  | 2.71 | 1.91 | 0.00 |
|  |  | 1.22 | 2.33 | 0.00 |

TABLE 3

ANTI-LHRH ANTIBODY RESPONSE MEASURED BY THE DEGREE OF BINDING OF IODINE-125-LABELLED LHRH
TESTING FOR ANTI-LHRH ANTIBODIES IN THE SERUM (DIL. 1/50)

| TIME (WKS.) | D-LYS6-LHRH-PDP-HSA/AE1 0.5 μg (A1) | | | | | D-LYS-LHRH-PDP-HSA/AE1 6 μg (A2) | | | | | TITER (B/T = 50%) A1 |
|---|---|---|---|---|---|---|---|---|---|---|---|
|  | No. pigs | | | | | No. pigs | | | | | No. pigs |
|  | 211 | 219 | 231 | 243 | 257 | 205 | 221 | 227 | 245 | 251 | 221 |
| T0 1st inj. |  |  |  |  |  |  |  |  |  |  |  |
| T3 | 0 | 0 | 0 | 0 | 0 | 0 | 71.8 | 0 | 0 | 0 | 150 |
| T4 | 0 | 0 | 0 | 0 | 0 | 0 | 67.3 | 0 | 0 | 0 | 100 |
| T5 2nd inj. | 0 | 0 | 0 | 0 | 0 | 0 | 53.4 | 0 | 0 | 0 | 50 |
| T6 | 0 | 0 | 0 | 0 | 0 | 14.2 | 58.5 | 42.1 | 6.6 | 0 | 55 |
| T7 | 0 | 0 | 0 | 0 | 0 | 7.5 | 48.5 | 36.7 | 5 | 0 | <50 |
| T8 | 0 | 0 | 0 | 0 | 0 | 7.7 | 44.1 | 28.8 | 5 | 0 | <50 |
| T9 | 0 | 0 | 0 | 0 | 0 | 5 | 37.5 | 22.6 | 5 | 0 | <50 |

| TIME (WKS.) | LHRH-(CARBO)-HSA/AE1 0.150 mg (B1) | | | | | LHRH-(CARBO)-HSA/AE1 1.2 mg (B2) | | | | | B1 | B2 |
|---|---|---|---|---|---|---|---|---|---|---|---|---|
|  | No. pigs | | | | | No. pigs | | | | | No. pigs | No. pigs |
|  | 213 | 225 | 247 | 255 | 261 | 209 | 215 | 235 | 241 | 259 | 247 | 235 | 259 |
| T0 1st inj. |  |  |  |  |  |  |  |  |  |  |  |  |
| T3 | 0 | 0 | 0 | 0 | 0 | 0 | 0 | 0 | 0 | 0 |  |  |
| T4 | 0 | 0 | 0 | 0 | 0 | 0 | 0 | 0 | 0 | 0 |  |  |
| T5 2nd inj. | 0 | 0 | 0 | 0 | 0 | 0 | 0 | 0 | 0 | 0 |  |  |
| T6 | 0 | 0 | 81.2 | 5 | 25.1 | 48.9 | 56.2 | 78.2 | 31.4 | 90.1 | 200 | 130 | 990 |
| T7 | 0 | 0 | 81.7 | 5 | 49.1 | 64.7 | 49.9 | 86.3 | 52.3 | 92.9 | 170 | 220 | 880 |
| T8 | 0 | 0 | 80.5 | 5 | 36.5 | 54.1 | 48.9 | 80.7 | 59.3 | 90.5 | 150 | 140 | 640 |
| T9 | 0 | 0 | 74.4 | 5 | 34.5 | 54.4 | 40.1 | 68.5 | 51.6 | 89.1 | 220 | 220 | 490 |

A2 - Comparative test of two anti-LHRH vaccines composed, respectively, of an LHRH-α-globulin conjugate with carbodiimide and a (D-LYS$^6$)-LHRH-α-globulin conjugate with SPDP, put into an oil-in-water emulsion and administered intramuscularly (IM) or transcutaneously (ID) in pigs.

A2.1 - Preparation of (D-Lys$^6$)-LHRH-α-globulin conjugate with SPDP

The method described in Example A1 is employed in exactly the same manner, but replacing albumin at a concentration of 10 mg/ml by α-globulin at a concentration of 6 mg/ml.

The overall yield of coupled (D-Lys$^6$)-LHRH is of the order of 45 to 50%.

Moreover, it is possible to modify at will the degree of substitution of the α-globulin, and hence the level of conjugation, by varying the SPDP and/or α-globulin concentrations during the preparation of the MP-α-globulin.

A2.2 - Preparation of LHRH-human α-globulin conjugate with carbodiimide (EDC).

The method described in Example A1 is employed in exactly the same manner, but replacing human albumin by human α-globulin. The level of conjugation is from 24 to 28 mg of LHRH bound per 100 mg of human α-globulin.

A2.3 - The efficacy of the vaccine based on the LHRH-α-globulin conjugate with carbodiimide is greater than the second one. The efficacy is expressed as the number of animals displaying a total disappearance of plasma testosterone (Table 4).

TABLE 4

|  | LHRH-α-glob. EDC (1.2 mg) IM + ID | (D-Lys$^6$)-LHRH-α-glob. SPDP (6 mg) IM + ID |
|---|---|---|
| Abolition of testosterone | 5/10 | 2/10 |

A.3 - Predominance of the immune response of male pigs to the carboxy-terminal fraction of the LHRH peptide conjugated with the carbodiimide, or of its agonist (D-Lys$^6$)-LHRH conjugated with SPDP, to human α-globulin:

This is determined by comparison of the percentages of binding of the anti-LHRH and anti-(D-Lys$^6$)-LHRH sera by two labeled LHRH fragments, LHRH (3–10) deleted in respect of its amino-terminal fraction, and LHRH (1–10) in free acid form and, as a result, deleted in respect of the amide fraction of its natural carboxyterminal fraction, respectively. These two fractions recognize, respectively, more especially antibodies directed towards the carboxy-terminal fraction on the one hand, and amino-terminal fraction on the other hand.

The predominance of the response to the carboxy-terminal fraction of the peptide manifests itself in the number of animals displaying antibodies binding only the peptide LHRH (3–10) to the exclusion of the binding of LHRH free acid (10/58 for the anti-LHRH serum and 3/10 for the anti-(D-Lys$^6$)-LHRH serum).

No serum showed 100% binding of the LHRH free acid fraction, which would reflect an exclusive recognition of the amino-terminal fraction.

The most frequent mixed responses show a better recognition of the amino-terminal fraction by the anti-(D-Lys$^6$)-LHRH sera than that of the anti-LHRH sera. In the latter, only 3 sera out of 58 have a recognition of greater than 40% of the amino-terminal fraction, against 4 out of 10 for the anti-(D-Lys$^6$)-LHRH serum.

B - Greater immunogenic activity of the LHRH-α-globulin conjugate produced with the carbodiimide compared to that obtained with the conjugate prepared with glutaraldehyde.

B.1 - Preparation of the LHRH-α-globulin conjugate with glutaraldehyde.

2.5 ml of glutaraldehyde solution containing 10 mg/ml are added dropwise and over a period of 30 min to 10 mg of LHRH and 50 mg of human α-globulin (Serra) dissolved in 5 ml of 0.1M phosphate buffer pH 7.5, stirring gently after each addition. After the mixture has been left for 2.5 h at room temperature, the reaction is stopped by adding 25 mg of sodium bisulfite dissolved in 0.5 ml of water. The conjugate is dialyzed at 4° C. against 150 mM NaCl mM phosphate buffer pH 7.5, and is concentrated by ultrafiltration.

B.2 - Comparative test on pigs of anti-LHRH vaccines formulated using identical amounts of conjugated LHRH. The efficacy is expressed as the number of animals displaying a total disappearance of plasma testosterone (Table 7).

TABLE 7

|  | LHRH-α-glo. with carbodiimide IM or ID administration | LHRH-α-glo. with glutaraldehyde IM or ID administration |
|---|---|---|
| Abolition of plasma testosterone | 5/10 | 0/10 |

C - Greater immunogenic activity of the conjugate employing human α-globulin compared to that obtained with the conjugate employing human serum albumin.

The efficacy is expressed as the number of animals displaying a total disappearance of plasma testosterone (Table 8).

TABLE 8

| Tests on pigs - intramuscular injection | | |
|---|---|---|
|  | LHRH-HSA with carbodiimide | LHRH-α-glo. with carbodiimide |
| Abolition of plasma testosterone | 0/5 | 3/5 |

D - Immunogenic activity of the conjugate employing equine α-globulin, fraction IV-i, equivalent to that obtained with the conjugate employing human α-globulin. D.1 - Preparation of the LHRH-equine α-globulin conjugate with carbodiimide.

The method described in Example A1 is employed in exactly the same manner, but replacing human albumin by equine α-globulin (fraction IV-1).

D.2 - Subcutaneous administration in rats, twice at an interval of 4 weeks, of a vaccine at a dose of 12 μg of LHRH conjugated to human or equine α-globulin.

TABLE 9

| Tests on rats | | |
|---|---|---|
|  | LHRH-human α-globulin fraction IV-1 with carbodiimide | LHRH-equine α-globulin fraction IV-1 with carbodiimide |
| Abolition of plasma testosterone | 12/12 | 12/12 |

E - Greater adjuvant activity of the water-in-oil emulsion of the invention over other emulsions (Table Tests on pigs employing the same conjugate composed of LHRH and human α-globulin with carbodiimide and administered at the same dose in the same volume transcutaneously at 5 points.

The emulsions examined are: a fluid oil-in-water emulsion (B), the emulsion of the invention (formula C in the table), a commercial emulsion to be diluted with the antigen (E) and an oily phase to be emulsified with the conjugate (F).

For all these formulae, the final amount of antigen per dose is the same.

The emulsions are produced under the customary conditions used by those specializing in formulations of this type.

TABLE 10

| Emulsions | B | C | E | F |
|---|---|---|---|---|
| Abolition of plasma testosterone | 2/5 | 4/4 | 1/5 | 3/5 |
| Number of animals displaying a tissue androstenone concentration below 0.5 µg/g | 2/5 | 4/4 | 3/5 | 3/5 |

F. Efficacy of passive anti-LHRH immunization for improving the organoleptic qualities of meat, measured by the lowering of tissue androstenone.

Table 11

Androstenone content of the adipose tissue in control animals and in those subjected to passive anti-LHRH immunoneutralization with a hyperimmune equine anti-(D-Lys$^6$)-LHRH plasma administered in a volume of 300 ml on days 16, 13, 9 and 5 before slaughter.

TABLE 11

Androstenone content of the adipose tissue in control animals and in those subjected to passive anti-LHRH immunoneutralization with a hyperimmune equine anti-(D-Lys$^6$)-LHRH plasma administered in a volume of 300 ml on days 16, 13, 9 and 5 before slaughter.

|  | Controls | Treated |
|---|---|---|
| Number of animals displaying an androstenone concentration below 0.50 µg/g of adipose tissue | 2/5 | 5/5 |

(significant difference at α-risk = 0.2)

G. - Efficacy and tolerability of the formulations containing LHRH conjugated to α-globulin with carbodiimide in the form of a water-in-oil emulsion (1st vaccine) and in aluminum hydroxide gel and saponin (2nd vaccine), administered transcutaneously at the same dose of conjugated LHRH, at the beginning of the fattening period and 18 to 21 days before slaughter, respectively, using a needleless injector known as Pigjet.

Two tests were performed in two stages, groups 1, 3 and 5 for the first and groups 2 and 4 for the second, respectively (Tables 12 and 13).

G.1 - The efficacy of anti-LHRH immunoneutralization is increased for an equal volume of vaccine by multiplication of the points of transcutaneous administration.

TABLE 12

| Groups | 1 | 2 | 3 | 4 | 5 |
|---|---|---|---|---|---|
| 1st vaccine | 1 ml (5 points) | 1 ml (5 points) | 1 ml (5 points) | 0.4 ml (10 points) | 0.4 ml (2 points) |
| 2nd vaccine | 1 ml (5 points) | 1 ml (5 points) | 0.4 ml (2 points) | 0.4 ml (10 points) | 0.4 ml (2 points) |
| Abolition of or marked decrease in testosterone (no. of animals) | 10/12 | 10/11 | 9/12 | 11/11 | 8/11 |
| Tissue androstenone concentration below 0.5 µg/g (no. of animals) | 11/12 | ND | 10/23 | ND | ND |

G.2 - Tolerance to the vaccines used is judged by the development of the inflammatory skin reaction, graded from 0 to 4 in an animal in accordance with the size of the papules appearing after administration; a papule appears at each administration point. The summation of the scores in each of the groups is summarized as follows: mean score at the end of the first week following administration (Ad. 1) and mean score at the time of slaughter for each of the vaccines (S1) (Table 13). The best tolerance is observed with the use of the vaccines in group 4.

TABLE 13

Tolerance on transcutaneous administration observed during the 2 tests performed (test 1 groups 1, 3 and 5, test 2 groups 2 and 4).

| Groups | 1 | | 2 | | 3 | | 4 | | 5 | |
|---|---|---|---|---|---|---|---|---|---|---|
| Vaccine 1 or 2 | 1st vac. | 2nd vac. | 1st vac. | 2nd vac. | 1st vac. | 2nd vac. | 1st vac. | 2nd vac. | 1st vac. | 2nd vac. |
| Number of administration points | 5 | 5 | 5 | 5 | 5 | 2 | 10 | 10 | 2 | 2 |
| Ad. 1 | 42 | 11 | 31 | 11 | 41 | 16 | 33 | 11 | 30 | 10 |
| S1 | 2 | 4 | 0 | 0 | 5 | 3 | 0 | 0 | 2 | 0 |
| Number of animals | 12 | | 11 | | 12 | | 11 | | 11 | |

II - Use of the Peptide (3-10)

A. Techniques of measurement of the anti-LHRH immune response and of the biological efficacy by the assay of plasma testosterone and tissue androsterone.

The anti-LHRH immune response is measured by the antibody titer which is determined according to the technique described by JEFFCOATE et al., Acto. Endocr. (Copenh.), 1974, 75, 625–635.

Bonding to the labelled peptides is determined after labeling the various peptides with iodine-125 according to COPPOLAND et al., Endocrinology, 1979, 104, 1504–1506. The determination of the sera with respect to these peptides is performed according to the technique of JEFFCOATE et el., cited above.

The biological efficacy is measured by the lowering or disappearance of plasma testosterone and tissue androstenone. The assay of plasma testosterone is performed directly on the plasma by an RIA technique employing the radioligand testosterone C19-carboxy methyl ether-[$^{125}$I]histamine. (FURUYAMA S. et al., Steroids, 1972, 16, 415). The assay of tissue androstenone is performed on a sample of adipose tissue by an RIA technique employing the radiologand 5α-[H]androstenone, desdribed by CLAUS, C.R. Acad. Sci., Paris, 1974. 278, 299–302.

B. Predominance of the immune response of male pigs to the carboxy-terminal fraction of the LHRH peptide conjugated with the carbodiimide, or of its agonist (D-Lys$^6$)-LHRH conjugated with SPDP, to human α-globulin.

B1. Preparation of the LHRH-human α-globulin conjugate with carbodiimide.

The conjugate is preferably obtained by adding from 0.5 to 2 volumes of a 2.5% solution of N-ethyl-N'-(3-dimethylaminopropyl)carbodiimide (EDC) hydrochloride in 0.9% NaCl to one volume of the α-globulin/LHRH mixture in solution containing 2 to 20 mg/ml in 0.9% NaCl. After stirring, the mixture is left overnight and then purified by gel permeation chromatography.

S2. Preparation of [(D-Lys$^6$)-LHRH]-human α-globulin conjugates with SPDP.

The preparation of [(D-Lys$^6$)-LHRH]-human α-globulin conjugates is carried out in 3 steps: preparation of {N-[3-(2-pyridyldithio)propanoyl]-D-Lys$^6$}-LHRH, preparation of N-(3-mercaptopropanoyl)-human α-globulin, then coupling.

{N-[3-(2-Pyridyldithio)propanoyl]-D-Lys$^6$}-LHRH is prepared by reacting an excess of SPDP with LHRH in aqueous solution (6 mol of SPDP per mole of (D-Lys$^6$)-LHRH), and then, after one night at 4° C., centrifuging the product obtained. The latter is dissolved in 8M urea and the 2-pyridyldithio groups present are assayed.

N-(3-Mercaptopropanoyl)-human α-globulin is obtained by the action of 0.2 mmol of SPDP on 0.6 μg of human α-globulin dissolved in 100 ml of 0.1M phosphate buffer, and then, after one night of contact at 4° C. and acidification to pH 6, by reduction with dithiothreitol. It is then purified by gel filtration chromatography. Assay of thiol and protein yields the average level of substitution.

Coupling is performed taking one 2-pyridyldithio group per 1.25 thiol groups. The pH is taken to 7–7.5 and then, after one hour, the yield is determined by measurement of the 2-pyridinethione liberated.

The average level of substitution is deduced from this. Finally, the conjugate is purified by chromatography and concentrated by ultrafiltration. The overall yield of coupled (D-Lys$^6$)-LHRH is of the order of 45 to 50%.

B3. The predominance of the immune response of male pigs to the carboxy-terminal fraction of the LHRH peptide conjugated under the conditions described in A1 and A2 is determined by comparison of the binding by the anti-LHRH and anti-(D-Lys$^6$)-LHRH sera of two labeled LHRH fragments, LHRH (3–10) (LHRH deleted in respect of its amino-terminal fraction), and LHRH (1–10) in free acid form (LHRH deleted in respect of the amide fraction of its carboxy-terminal fraction), respectively. These two fractions recognize more especially antibodies directed, respectively, towards the carboxy-terminal fraction on the one hand, and amino-terminal fraction on the other hand.

The response to the carboxy-terminal fraction of the peptide is general in all the animals immunized with one or other of the conjugates (68/68). The sera of 3 out of 10 of the 10 animals immunized with conjugated (D-Lys$^6$)-LHRH and of 10 out of 68 of the animals immunized with conjugated LHRH showed exclusively a binding of the carboxy-terminal fraction. The other animals display a mixed response preferentially directed towards the carboxy-terminal fraction.

The response to the amino-terminal fraction is not general (55/68). No serum showed binding exclusive to the LHRH free acid fraction.

C. Tests of active anti-LHRH immunoneutralization using LHRH (3–10)-equine α-globulin IV-4 and LHRH (3–10)-ovalbumin conjugates produced with carbodiimide.

C1. Preparation of the LHRH (3–10)-equine α-globulin IV-4 conjugate with carbodiimide.

Eighty-five mg of LHRH (3–10) and 170 mg of equine α-globulin IV-4 are dissolved in 12.8 ml of 0.1M NaCl/0.1M 2-(N-morpholino)ethanesulfonic acid buffer. 212 mg of N-ethyl-N'-(3-dimethylaminopropyl)carbodiimide hydrochloride, dissolved in 17 ml of the above solution, are then added. The pH is immediately adjusted to 6.0 by adding 1.3 ml of 1N sodium hydroxide.

After stirring, the mixture is left for 16 h at room temperature, and the conjugate is then purified by gel permeation chromatography to separate the conjugate from unconjugated LHRH. Measurement of the amount of the latter enables the amount of LHRH coupled to be obtained by difference. It is possible to determine the coupling yield.

C2. Preparation of the LHRH (3–10)-ovalbumin conjugate with carbodiimide.

Sixty mg of LHRH (3–10) and 120 mg of ovalbumin are dissolved in 9 ml of 0.1M NaCl/0.1M 2-(N-morpholino)-ethanesulfonic acid buffer. 150 mg of N-ethyl-N'-(3-dimethylaminopropyl)-carbodiimide hydrochloride, dissolved in 12 ml of the same buffer, are then added. The pH is adjusted to 7.0 by adding 1N sodium hydroxide (approximately 1.9 ml). The mixture is left overnight at room temperature and is then clarified by centrifugation. The supernatant is chromatographed on Sephadex gel to separate the conjugate from unreacted LHRH and products originating from the initial carbodiimide. By measurement of the amount of unbound LHRH (3–10), it is possible to determine the coupling yield of LHRH (3–10).

C3. Immune response, biological efficacy and tolerance to the anti-LHRH vaccine formulated from the conjugate obtained between the fragments LHRH (3–10) and equine α-globulin IV-4 with carbodiimide.

The formulations, consisting of conjugated LHRH (3–10) put into the form of a water-in-oil emulsion (1st vaccine) and into an aluminum hydroxide gel and saponin (2nd vaccine), were administered transcutaneously to 6 male pigs in a volume of 0.4 ml per dose, at the beginning of the fattening period and 17 days before slaughter, respectively, using a needleless injector known as Pigjet delivering the dose volume in two applications of 0.2 ml distributed at 5 points at each application.

The immune response was maximal 10 days after administration of the 2nd vaccine. The individual antibody titers (reciprocal of the dilution at which iodine125 is 50% bound) were, respectively:

Day 10 280 660 2,700 3,200 4,600 13,000
Day 16 290 400 2,000 2,400 3,100 8,600

The biological efficacy of this immune response manifests itself in the disappearance of plasma testosterone from day 10 after administration of the 2nd vaccine in all 6 animals. The disappearance of testosterone is accompanied, under the same conditions, by the disappearance of tissue androstenone.

Tolerance to the vaccine is judged by the development of the inflammatory skin reaction, graded in accordance with the size of the papules appearing at each point of delivery of the vaccine after administration. This local inflammation has completely disappeared from day 10 after administration of the 2nd vaccine.

We claim:

1. A method for the production of meat having improved organoleptic qualities, comprising the fattening of uncastrated male animals selected from the group consisting of cattle, sheep and pigs, and possessing androgenic steroids and non-androgenic steroids, while permitting the development of the male character of said animals and shortly before slaughter of said animals subjecting said animals to anti-LHRH active immunoneutralization to substantially abolish the action of said androgenic and non-androgenic steroids only shortly before slaughter, the method comprising one administration before or during the fattening of the animals of an anti-LHRH vaccine designed to induce a primary, low-intensity immune response without a significant or even measurable effect on gonadal steroid secretion to permit the development of the male character of the animals and then, shortly before slaughter, the administration of an anti-(LHRH) vaccine, to induce an anti-LHRH immunoneutralization substantially abolishing the action of the androgenic and non-androgenic steroids.

2. The method as claimed in claim 1, wherein the anti-LHRH vaccine administered first is administered before the phase of fattening of the animal.

3. The method as claimed in claim 2, wherein the vaccine in emulsion form is a vaccine in the form of a water-in-oil emulsion.

4. The method as claimed in claim 3, wherein the water-in-oil emulsion is made from a mixture of highly purified mineral oils and of nonionic surfactants.

5. The method as claimed in claim 1, wherein the anti-LHRH vaccine administered first is a vaccine in emulsion form.

6. The method as claimed in claim 1, wherein, the animals are pigs, and the anti-LHRH vaccine is administered before slaughter with an aqueous type adjuvant.

7. The method as claimed in claim 6, wherein the aqueous type adjuvant is chosen from the group consisting of aluminum hydroxide gel, saponin and a mixture of aluminum hydroxide and saponin.

8. The method as claimed in claim 6, wherein the vaccine is administered in an aqueous adjuvant from 15 to 21 days before slaughter.

9. The method as claimed in claim 1, wherein, the animals are cattle and sheep, and an anti-(LHRH) vaccine is administered before slaughter with an adjuvant in emulsion form.

10. The method as claimed in claim 9, wherein the vaccine in emulsion form is administered from one to two months before slaughter.

11. The method as claimed in claim 9, wherein the vaccine in emulsion form is administered from four weeks to several months after the administration carried out first.

12. The method as claimed in claim 1, wherein the anti-LHRH vaccine comprises an LHRH coupled to an immunogenic carrier protein chosen from the group consisting of:

bovine serum albumin,
human serum albumin
thyroglobulin,
ovalbumin
anatoxins,
tetanus anatoxin,
equine globulins,
human globulins.

13. The method as claimed in claim 12, wherein the administration is performed transcutaneously, using a needleless injection apparatus, via a jet under pressure.

14. The method as claimed in claim 1, wherein the conjugate comprises, LHRH, coupled to an immunogenic carrier protein chosen from the group consisting of equine alpha-globulin, equine alpha-globulin fraction IV-1, equine alpha-globulin fraction IV-4 and a mixture thereof.

15. The method as claimed in claim 14, wherein the peptide and immunogenic carrier protein are coupled with a carbodiimide.

16. The method as claimed in claim 1, wherein the conjugate comprises LHRH (3–10) which is coupled to an immunogenic carrier protein chosen from the group consisting of ovalbumin, equine alpha-globulin, equine alpha-globulin fraction IV-1, equine alphaglobulin fraction IV-4 and a mixture of these fractions.

17. The method as claimed in claim 16, wherein the peptide and immunogenic carrier protein are coupled with a carbodiimide.

18. The method of claim 1 wherein the administration is performed transcutaneously at several points using a needleless injection apparatus via a jet under pressure.

* * * * *

UNITED STATES PATENT AND TRADEMARK OFFICE
CERTIFICATE OF CORRECTION

PATENT NO. : 5,573,767
DATED : November 12, 1996
INVENTOR(S) : Dufour et al.

It is certified that error appears in the above-identified patent and that said Letters Patent is hereby corrected as shown below:

Title page: item [73] should read as follows:
-- [73] Assignee: Rhone Merieux, Societe Anonyme --

Claim 3, line 1, delete "2" and insert therefor --5--

Signed and Sealed this

Fifteenth Day of August, 2000

Attest:

Q. TODD DICKINSON

Attesting Officer

Director of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 10
        ( D ) OTHER INFORMATION: /label=NH2
            / note="amidated glycine"

( i x ) FEATURE:
        ( A ) NAME/KEY: Peptide
        ( B ) LOCATION: 1
        ( D ) OTHER INFORMATION: /label=pyro
            / note="pyroglutamic acid"

( x ) PUBLICATION INFORMATION:
        ( A ) AUTHORS: Matsuo, H.
            Baba, Y.
            G. Nair, R. M.
            Arimura, A.
            Schally, A. V.
        ( B ) TITLE: Structure of the porcine LH- and
            FSH- releasing hormone. I. The proposed amino acid
            sequence.
        ( C ) JOURNAL: Biochem. Biophys. Res. Commun.
        ( D ) VOLUME: 43
        ( E ) ISSUE: 6
        ( F ) PAGES: 1334-1339
        ( G ) DATE: 1971
        ( K ) RELEVANT RESIDUES IN SEQ ID NO:1: FROM 1 TO 10

( x i ) SEQUENCE DESCRIPTION: SEQ ID NO:1:

Glu His Trp Ser Tyr Gly Leu Arg Pro Gly
        1                  5                         10

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 8
        ( D ) OTHER INFORMATION: /label=NH2
            / note="amidated glycine"

(x) PUBLICATION INFORMATION:
  (A) AUTHORS: Schally, A. V.
              Arimura, A.
              Carter, W. H.
              Redding, T. W.
              Geiger, R.
              Konig, W.
              Wissman, H.
              Jaeger, G.
              Sandow, J.
              Yanaihara, N.
  (B) TITLE: Luteinizing hormone- relaesing hormone (LH-RH)
             activity of some synthetic polypeptides. I.
             Fragments shorter than decapeptide.
  (C) JOURNAL: Biochem. Biophys. Res. Commun.
  (D) VOLUME: 48
  (E) ISSUE: 2
  (F) PAGES: 366-375
  (G) DATE: 1972
  (K) RELEVANT RESIDUES IN SEQ ID NO:2: FROM 1 TO 8

(xi) SEQUENCE DESCRIPTION: SEQ ID NO:2:

Trp  Ser  Tyr  Gly  Leu  Arg  Pro  Gly
 1               5